United States Patent
Rakshit et al.

(10) Patent No.: US 10,381,956 B1
(45) Date of Patent: Aug. 13, 2019

(54) WIRELESS CHARGING COIL IN CLOTHING

(71) Applicant: International Business Machines Corporation, Armonk, NY (US)

(72) Inventors: Sarbajit K. Rakshit, Kolkata (IN); Harish Bharti, Pune (IN); Abhay Patra, Pune (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/152,269

(22) Filed: Oct. 4, 2018

(51) Int. Cl.
| | |
|---|---|
| *A41D 1/00* | (2018.01) |
| *H02N 2/18* | (2006.01) |
| *H01L 41/113* | (2006.01) |
| *H02J 7/02* | (2016.01) |
| *G06Q 30/02* | (2012.01) |
| *A61B 5/00* | (2006.01) |
| *A61B 5/11* | (2006.01) |
| *G01P 13/00* | (2006.01) |

(52) U.S. Cl.
CPC ............ *H02N 2/18* (2013.01); *A41D 1/002* (2013.01); *G06Q 30/0204* (2013.01); *H01L 41/113* (2013.01); *H02J 7/025* (2013.01); *A61B 5/11* (2013.01); *A61B 5/6804* (2013.01); *G01P 13/00* (2013.01)

(58) Field of Classification Search
CPC ...... H02N 2/18; A41D 1/002; G06Q 30/0204; H02J 7/025; H01L 41/113; G01P 13/00; A61B 5/11; A61B 5/6804
See application file for complete search history.

(56) References Cited

U.S. PATENT DOCUMENTS

| | | | |
|---|---|---|---|
| 2014/0180624 A1* | 6/2014 | Nikonov | G01K 7/16 702/130 |
| 2014/0217853 A1 | 8/2014 | Mankowski | |
| 2017/0180535 A1* | 6/2017 | Esenwein | H02J 50/20 |
| 2018/0289189 A1* | 10/2018 | Lazzi | A47G 25/14 |
| 2018/0343930 A1* | 12/2018 | Alipour | A41D 1/002 |

OTHER PUBLICATIONS

Florian Schumacher, "Energy Harvesting for Wearables," WT Wearable Technologies Conference, [Accessed Online Oct. 3, 2018] http://www.electronics-eetimes.com/news/woven-piezoelectric-yarns-lead-3d-textile-energy-harvester https://www.wearable-technologies.com/2014/07/energy-harvesting-for-wearables/.

(Continued)

*Primary Examiner* — Daniel J Cavallari
(74) *Attorney, Agent, or Firm* — Patterson + Sheridan, LLP

(57) ABSTRACT

The embodiments describe monitoring user activity to estimate the amount of power generated by piezoelectric fabric disposed in an article of clothing, where the piezoelectric fabric is configured to generate electrical energy in response to user movement that is stored in a power supply device, and where the power supply device is configured to provide power to a charging coil disposed in the article of clothing for charging an electronic device. Upon determining the estimated power is insufficient to charge the electronic device to a threshold power level, a user exercise is selected which is predicted to generate sufficient power using the piezoelectric fabric to reach the threshold power level. A prompt is outputted to the user to perform the user exercise.

20 Claims, 5 Drawing Sheets

(56) References Cited

OTHER PUBLICATIONS

Yring Malin, "Textile Integrated Introduction: Investigation of Textile Inductors for Wireless Power Transfer," University of Boras, Faculty of Textiles, Engineering and Business, 2016, 75 pages.
Farag, Tasabeeh Khalid Mohamed, "Human Generated Power by Using Piezoelectric Transducer," SUST Repository, 2016.
Christopher Pastore, "Development of Energy Generating Textiles & Fabrics—by Hugh Carter Donahue & Christophe Pastore," [Accessed Online Oct. 3, 2018] http://www.2greenenergy.com/2012/07/23/development-of-energy/.

\* cited by examiner

WIRELESS CHARGING COIL IN CLOTHING

BACKGROUND

This disclosure relates generally to computer systems and, more particularly, relates to distributing electronic charging devices in clothing.

Battery-powered devices often need to be charged frequently. The amount of battery-powered devices such as mobile phones, smart watches, and other portable electronic devices used by society is increasing. Charging these devices often require the user to plug the device into a wall charger, which means the device can no longer be carried by the user. That is, the batter-powered devices cannot be charged on the go, while being carried by the user. As the use of battery-powered devices increases, being able to provide flexible and dynamic techniques to charge electronic devices has become more important.

SUMMARY

Methods and systems for distributing electronic devices on clothing worn by users are provided, where the distribution is based on information related to user activity, where profiles can be determined based on user activity, and where, in one or more embodiments, the profiles serve as the basis for the distribution of the electronic devices in the clothing and the generation of advertisements for the same.

According to one embodiment of the present disclosure a method is provided. The method includes: receiving data associated with physical activity of a user, distributing a plurality of piezoelectric charging devices on clothing worn by the user based on the received user activity data, wherein each one of the plurality of piezoelectric charging devices is located at a separate location on the clothing, providing a power supply device for the article of clothing to deliver power to an electronic device contacting the clothing, where the power supply device forms a circuit with the at least one of the plurality of piezoelectric charging devices, where the plurality of piezoelectric charging devices are powered by movement by the user, and where the power supply receives the power from the plurality of piezoelectric charging devices, and delivering power to the electronic device via the plurality of piezoelectric charging devices.

Another embodiment of the present disclosure includes a system. The system includes: an activity data collector for receiving data associated with physical activity of a user, an activity analysis component for distributing a plurality of piezoelectric charging devices on clothing worn by the user based on the received user activity data, wherein each one of the plurality of piezoelectric charging devices is located at a separate location on the clothing, a power supply device to deliver power to an electronic device contacting the clothing, where the power supply device forms a circuit with the at least one of the plurality of piezoelectric charging devices, where the plurality of piezoelectric charging devices are powered by movement by the user, and where the power supply receives the power from the plurality of piezoelectric charging devices and transmits the power to the electronic device.

Yet another embodiment of the present disclosure includes a computer program product for charging wearable material. The computer program product includes: a computer-readable storage medium having computer-readable program code embodied therewith, the computer-readable program code executable by one or more computer processors to: receive data associated with physical activity of a user, distribute a plurality of piezoelectric charging devices on clothing worn by the user based on the received user activity data, wherein each one of the plurality of piezoelectric charging devices is located at a separate location on the clothing, provide a power supply device for the article of clothing to deliver power to an electronic device contacting the clothing, where the power supply device forms a circuit with the at least one of the plurality of piezoelectric charging devices, where the plurality of piezoelectric charging devices are powered by movement by the user, and where the power supply receives the power from the plurality of piezoelectric charging devices, and deliver power to the electronic device via the plurality of piezoelectric charging devices.

DETAILED DESCRIPTION

Mobile devices, such as cell phones and smart watches, are in constant use in modern life. Since these devices have a finite battery life, and since charging stations are not always accessible and/or convenient to user, having an ability to charge these devices on the go is advantageous. One or more embodiments of the present disclosure provide distribution of charging devices on clothing so that the mobile electronic equipment can be charged whenever necessary by a user, and in the way that coincides with a user's particular life style.

Figure 1A:
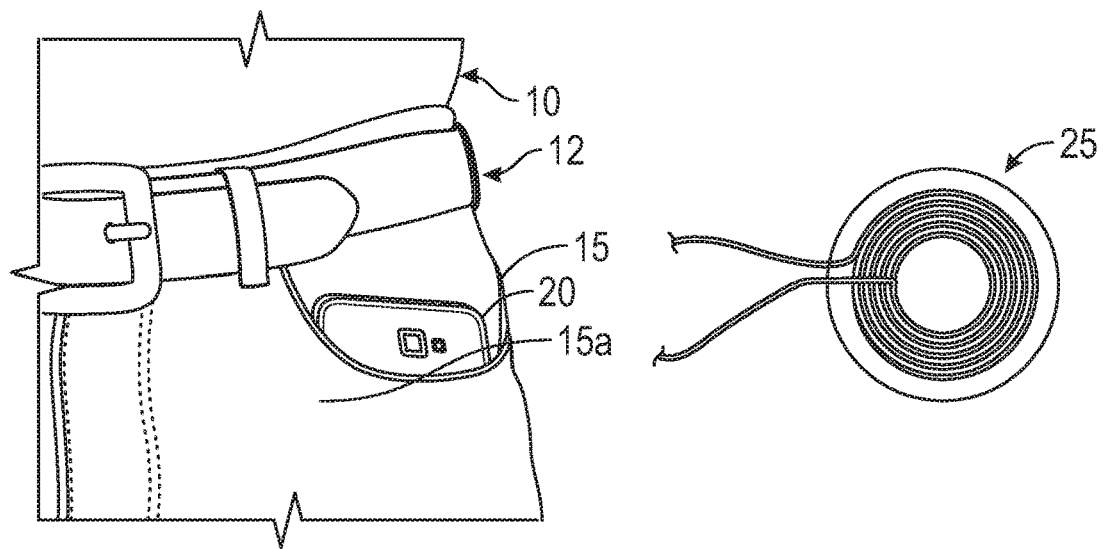
FIG. 1A illustrates one or more charging devices embedded in clothing of a user according to an embodiment of the present disclosure.

FIG. 1A illustrates an example of a charging device 25 located on an article of clothing and for charging an electronic device 20. A portion of the user's body is shown, where the user is wearing multiple articles of clothing, e.g. pants 12 and a shirt 10. A portion of the clothing has an area (e.g., a pocket) that can contain the electronic device 20, e.g. a cell phone. In one embodiment, a subsection 15a of the clothing is configured or manufactured to contain a charging device 25, such as piezoelectric fabric connected to a charging coil that can be used to charge the electronic device 20 using power generated by user movement.

In one embodiment, piezoelectric fabric can be integrated into the charging device 25 along with the charging coil. However, in other embodiments, the clothing can include multiple patches of piezoelectric fabric (which can include piezoelectric thread), which are separate from the charging devices 25, that generate electricity (or power) as the user moves. For example, the piezoelectric fabric may be disposed at portions of the clothing that experience large amount of movement as the user moves such as knee or elbows and are connected to the charging device 25 using electrical wires. Moving the clothing results in the piezoelectric fabric generating electricity which can be routed to the charging coils in the charging devices 25 (if the charging devices 25 are currently charging the electronic device 20) or to a battery (not shown) so the energy can be stored for later use.

Figure 1B:
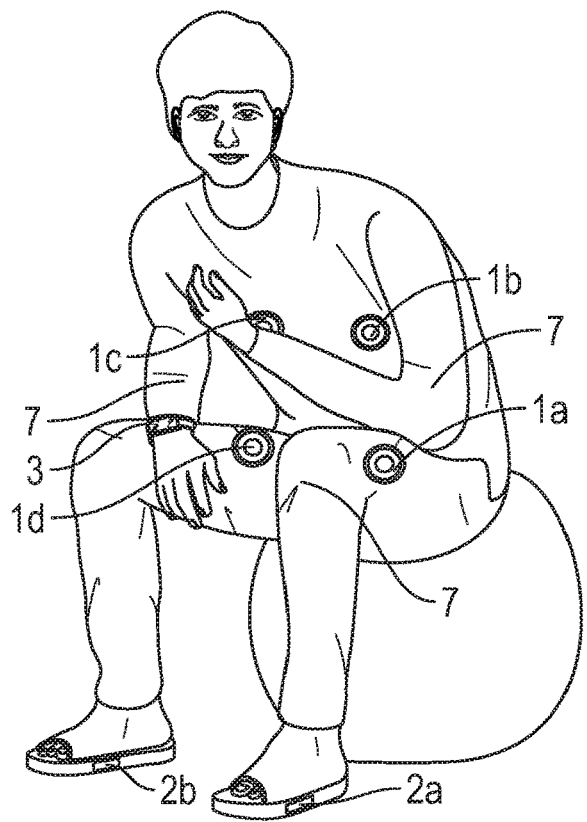
FIG. 1B illustrates one or more charging devices embedded in clothing of a user according to an embodiment of the present disclosure.

FIG. 1B illustrates a distribution of charging devices 1*a*-1*d* on multiple articles of clothing of a user. The charging devices 1*a* and 1*d* are located on the pants of the user and the charging devices 1*b* and 1*c* are located on the shirt of the user. The distribution of the charging devices can be allocated based on known movements of the user and the types of electronic devices that the user intends to charge. For example, the user, as shown, is sitting with an electronic watch 3 attached to his wrist, and the charging device 1*d* can thus serve as a charging station when the user moves his wrists towards his body along the pants. The charging devices 1*b* and 1*c* can be used to charge the watch 3 as the user brushes up against his shirt when walking or in a stationery position. For example, one movement of the user is to rest his hand/wrist (and as such electronic device 3) upon a portion of his chest (and thus in contact with charging devices 1*b* and 1*c*). This distribution and pose by the user is exemplary, and other distributions are possible based on the teachings of the present disclosure.

In one embodiment, one or more power supplies, e.g. batteries, 2*a*, 2*b* are in the articles of clothing containing the charging devices, e.g. 1*b*, 1*c*, or on another article of clothing. For example, as show in FIG. 1B, the batteries 2*a*, 2*b* can be located on the shoe of the user which are then electrically connected to the charging devices 1*a*-1*d*. The batteries store electrical energy provided from patches of piezoelectric fabric which may be part of the charging devices 1*a*-1*d* (when they are not currently charging an electronic device but are nonetheless generating electricity based on user movements) or separate therefrom. In FIG. 1B, patches of piezoelectric fabric 7 are disposed separate from the charging devices 1*a*-1*d* and are located on portions of the clothes most likely to be bent or ruffled when the user moves (e.g., knees, elbows, wrists, etc.). The patches of piezoelectric fabric 7 can directly provide power to the charging devices 1*a*-*d* to charge the electronic device 3 or deliver power to the batteries 2*a*, 2*b* which in turn deliver power to the charging devices 1*a*-1*d* for charging the external electronic device 3.

Figure 2:
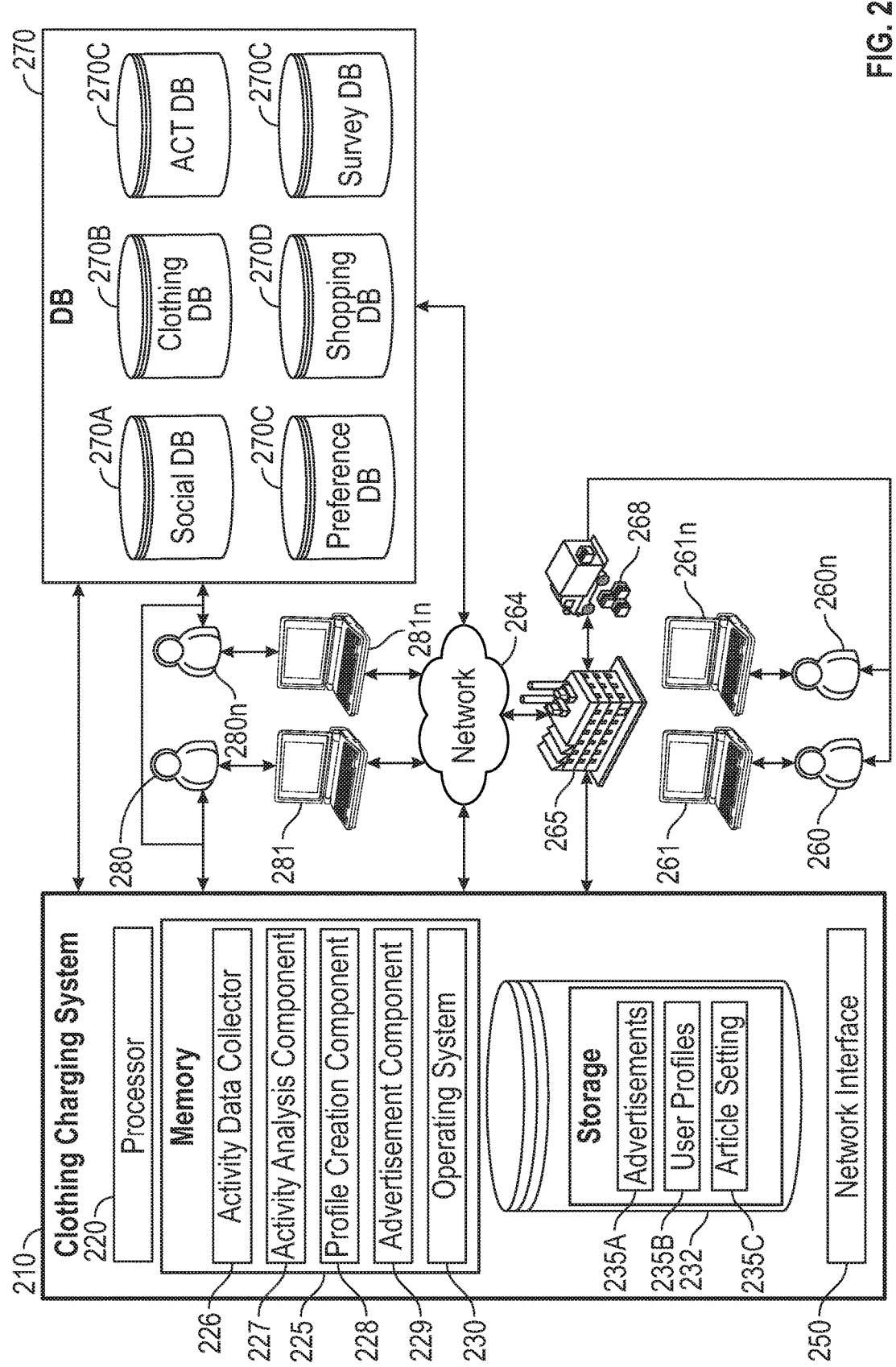
FIG. 2 illustrates a system for distributing one or more charging devices in clothing of a user according to an embodiment of the present disclosure.

FIG. 2 illustrates a system 200 for distributing charging devices on clothing for one or more users. The system 200 includes one or more hardware or software components for carrying out one or more operations for distributing the charging devices, including a clothing charging system 210. The clothing charging system 210 includes a processor 220 and one or more components stored in memory 225. The components include an activity data collector 226, an activity analysis component 227, a profile creation component 228, an advertising component 229, and an operating system 230 (where the operating system 230 can be any suitable operating system). The components of the system 200, including charging system 210, communicate with one another via a suitable network 264, e.g. such as a local area network (LAN), a general wide area network (WAN), an entity intranet, and/or a public network (e.g. internet). The clothing charging system 210 interfaces with the network 264 using any suitable network interface 250. One or more users 260, 260*n* 280, and 280*n*, using computer devices 261, 261*n*, 281, and 281*n* can interact with the clothing charging system 210 via the network 264. The activity data collector 226 collects data about the one or more users 260, 260*n*, 280, and 280*n* from one or more sources, including but not limited to external databases 270 and/or the one or more users 260, 260*n*, 280, and 280*n* themselves. The external databases 270 includes i) a social media database 270*a* with social media information, including a social medial profile, for each of the one or more users 260, 260*n*, 280, and 280*n*, ii) a clothing database 270*b* with information about various articles of clothing, including various distribution for charging devices for clothing, iii) an account database 270*c* that includes professional and miscellaneous information about the one or more users 260, 260*n*, 280, and 280*n*, including activity information such as gym memberships, exercise regiments, and physical capabilities, iv) a preference database 270*d* that includes information about the physical activity, social, professional, and personal information of one or more users 260, 260*n*, 280, and 280*n*, v) a shopping database 270*e* that includes the shopping habits of the one or more users 260, 260*n*, 280, and 280*n*, including the types of electronic devices they are interested in and the types of clothing they are interested in, e.g. a shopping history for electronic devices and clothing for one or more users 260, 260*n*, 280, and 280*n*, and vi) a survey database 270*f* that includes responses directly provided by the one or more users 260, 260*n*, 280, and 280*n* with respect to the types of clothing they are interested in, the types of electronic devices they are interested in, the distribution of charging devices they would be interested in with respect to clothing, and/or the types of the physical activity they engage in.

The activity data collector 226 can collect information for one or more users 260, 260*n*, 280, and 280*n* from the one or more external databases 270. The activity analysis component 227 analyzes the information collected by the activity data collector 226 to determine a distribution of charging devices for one or more articles of clothing and for charging one or more electronic devices, e.g. as shown in FIG. 1A and FIG. 1B. The distribution can be specific to a particular user, e.g. 281, based on information that is specific to that user, e.g. information about the physical and professional activity unique to that user, such as his or her career, activity associated with that career, and daily exercise routine (at a gym or otherwise).

The profile creation component 238 can coordinate with the activity analysis component 227 to develop one or more profiles for a large number of users, e.g. 280, 280*n*. The profile can be based on analyzing data for a large number of users to develop specific profiles that have common attributes in terms of the types of electronic devices used, the type of clothing typically worn by users that share that common profile, and optimal distribution of charging devices based on the profile. For example, a profile of users that share a type of job that entails significant amount of physical activity, e.g. police officer or athlete with a common set of contact points as a result of the physical activity, may benefit from a certain type of clothing and one kind of charge device distribution, whereas a more sedentary profile, e.g. a lawyer or accountant, may better served using a different charge device distribution.

In one embodiment, the advertising component 239 generates advertisements for clothing with profile specific distributions and advertises them to users 260, 260n that have an online shopping patter or social medial profile that suggests that the users 260, 260n have an activity regiment that matches a particular profile.

The advertisements 235A, the user profiles 235B, and the distribution of charging devices on particular clothing 235C can be stored in storage 232.

The system 210 can communicate with a manufacturing center 265 to provide instructions and templates for making clothing that aligns with a user profile 235 or a piece of clothing that is unique to an individual. One or more users 260, 260n, in response to an advertisement 235A, or as a result of independently initiated shopping activity, can order an article of clothing from a distribution facility 268 that communicates with the manufacturing center 265.

Figure 3A:
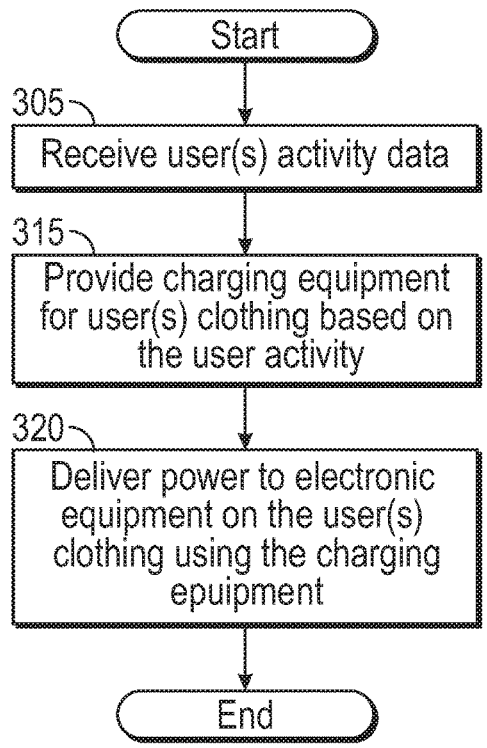
FIG. 3A illustrates a flow for distributing one or more charging devices in clothing of a user according to an embodiment of the present disclosure.

FIG. 3A illustrates a flow 300A for distributing charging devices 25, on one or more articles of clothing, e.g. 12. Per block 305, the activity data collector 226 receives data from one or more sources, such as external databases 270, about physical activity of one or more users, e.g. 280, 280n. In one embodiment, per block 310, the activity analysis component analyzes the received data and provides a distribution of charging devices 25 to a piece of clothing that is specific to a user 280 activity. Per block 310, the activity analysis component will also provide a location, for the same piece of clothing or a different piece of clothing, to contain a power supply to receive power from the charging devices 25 and power electronic devices in contact with the user, e.g. 280. In one embodiment, the power supply device forms a circuit with the at least one of the plurality of charging devices 25 where piezoelectric fabric generates electricity using the movement by the user 280 which is routed to the charging devices 25, or the power supply receives the power from the piezoelectric fabric, and, per block 315, delivers the power to the electronic device via the plurality of charging devices.

Figure 3B:
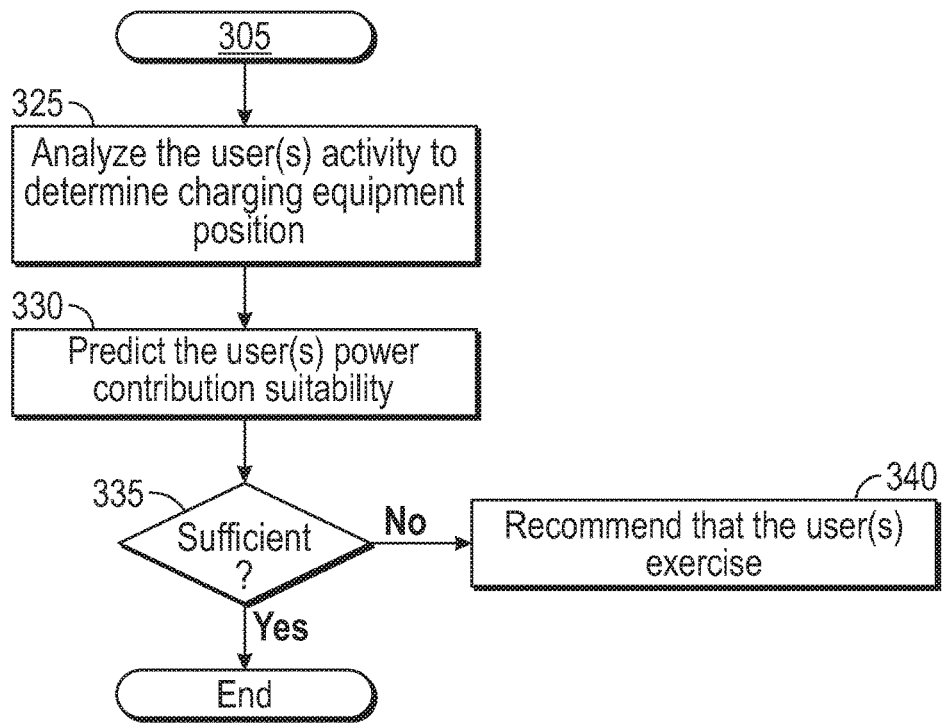
FIG. 3B illustrates a system for distributing one or more charging devices in clothing of a user according to an embodiment of the present disclosure.

FIG. 3B illustrates a flow 300A for distributing charging devices, on one or more articles of clothing. The flow starts at block 305. Per block 325, the activity analysis component 227 analyzes the data concerning user activity to recommend specific positions on the clothing that are predicted to maximize charging effectiveness and charging accessibility for an electronic device (or more than one device) carried by the user. In block 330, based on the information received concerning the user 280, the activity analysis component 227 can determine whether the user 280 is sufficiently active to charge the electronic device at a particular time during the day or as a general matter throughout the day. In block 335, if the activity is sufficient to charge the electronic device, the flow ends. If not, then the flow proceeds to block 340, and the activity analysis component provides the user with a suggested exercise or activity regiment, that is suitable for that user based on the received user activity data, so as to be able to sufficiently charge the electronic device or electronic devices.

Figure 4A:
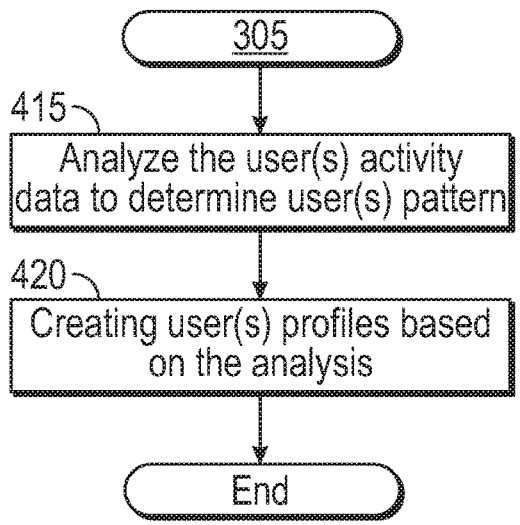
FIG. 4A illustrates a system for distributing one or more charging devices in clothing of a user according to an embodiment of the present disclosure.
Figure 4B:
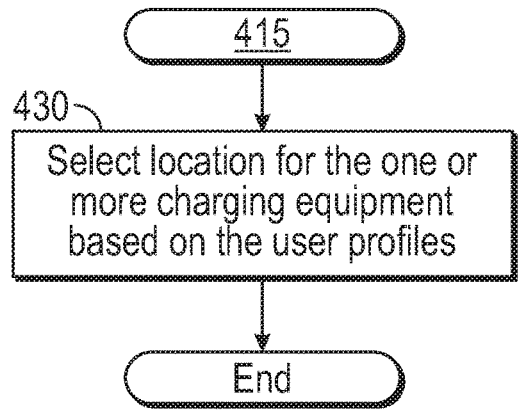
FIG. 4B illustrates a system for distributing one or more charging devices in clothing of a user according to an embodiment of the present disclosure.

FIG. 4A and FIG. 4B illustrate flows 400A and 400B, respectively, for distributing charging equipment on clothing and performing other operations concerning the same in accordance with one or more embodiments of the present disclosure. The flow for 400A begins at 305, where the received data included data for more than one users 280, 280n. The activity analysis component 227 analyzes the user activity for multiple users to determine a common pattern based on a profession, hobby, physical fitness regiment, etc. and coordinate with the profile creation component 238, where the profile creation component creates one or more user profiles that can serve as the basis for one or more generic clothing patterns with charging devices that can be mass produced. In one embodiment, the sources used to ascertain the patterns or profiles are outlined above, and can include i) a social media profile of each of the users, ii) a data source containing a shopping history for each the users, and iii) survey data collected from of each of the users. The ascertained patterns or profiles determined from the sources, as stated or implied, can include: i) a professional pattern (physical activity based on the type of work done by a user, e.g. police officer), ii) a hobby pattern (physical activity done based on a hobby, e.g. hiking), and iii) a preference pattern (physical activity and poses relevant to a user that are based on common preferences in how one or more users go about the day). In flow 400B, the flow beings at block 415, and per block 430, the profile creation component 238 provides one or more templates with particular distributions for charging devices and/or power supplies based on the user profiles.

Figure 5:
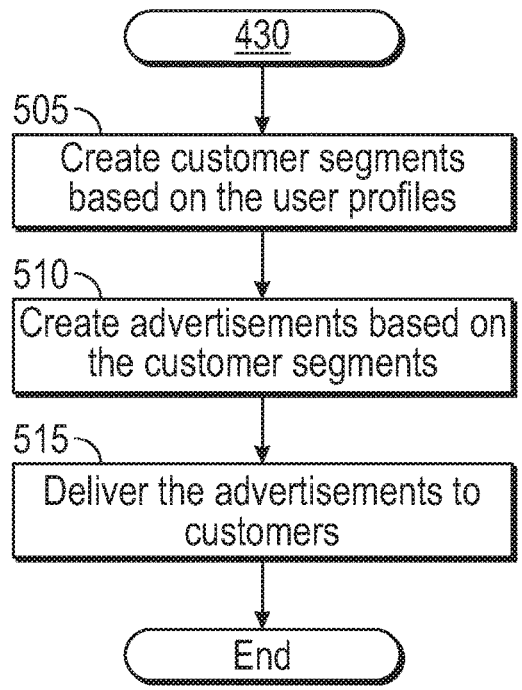
FIG. 5 illustrates a system for distributing one or more charging devices in clothing of a user according to an embodiment of the present disclosure.

FIG. 5 illustrates flow 500 for generating and providing advertisements to users for clothing with electronic devices based on user profiles in accordance with at least one embodiment of the present disclosure. The flow begins at block 430. At block 505, in coordination with the activity analysis component 227, the profile creation component 238 analyzes various information about shoppers, e.g. users 260, 260n, including social medial information, shopping history, and/or direct survey information to create one or more customer segments that align with the created profiles. For example, one customer segment may be for clothing that is for hikers, and that has charging equipment in the clothing based on hiking activity (e.g., the piezoelectric fabric is disposed at the knees to generate electricity as the hiker steps), whereas another group will be clothing for office workers, where the charging device distribution is better suited for the type activity and poses associated with office work (for example, the piezoelectric fabric may be disposed at the wrist to generate electricity from a user typing on a keyboard). In block 510, once the customer segments are created by the profile creation component 238, the profile creation component 238 coordinates with the advertisement generation component 239. The advertisement generation component 239 provides advertisements to the users 260, 260n based on the created customer segment, where the advertising is based on activity indicated in the profiles associated with the segments, e.g., hiker clothing advertising for hikers and office worker clothing for office workers. The advertisement generation component 239 delivers the advertisement to the users 260, 260n who can place an order for a particular piece of clothing with charging devices via a distribution facility 268 or organization, which directly manufactures the clothing, or receives it from one or more manufacturing facilities 265.

Figure 6:
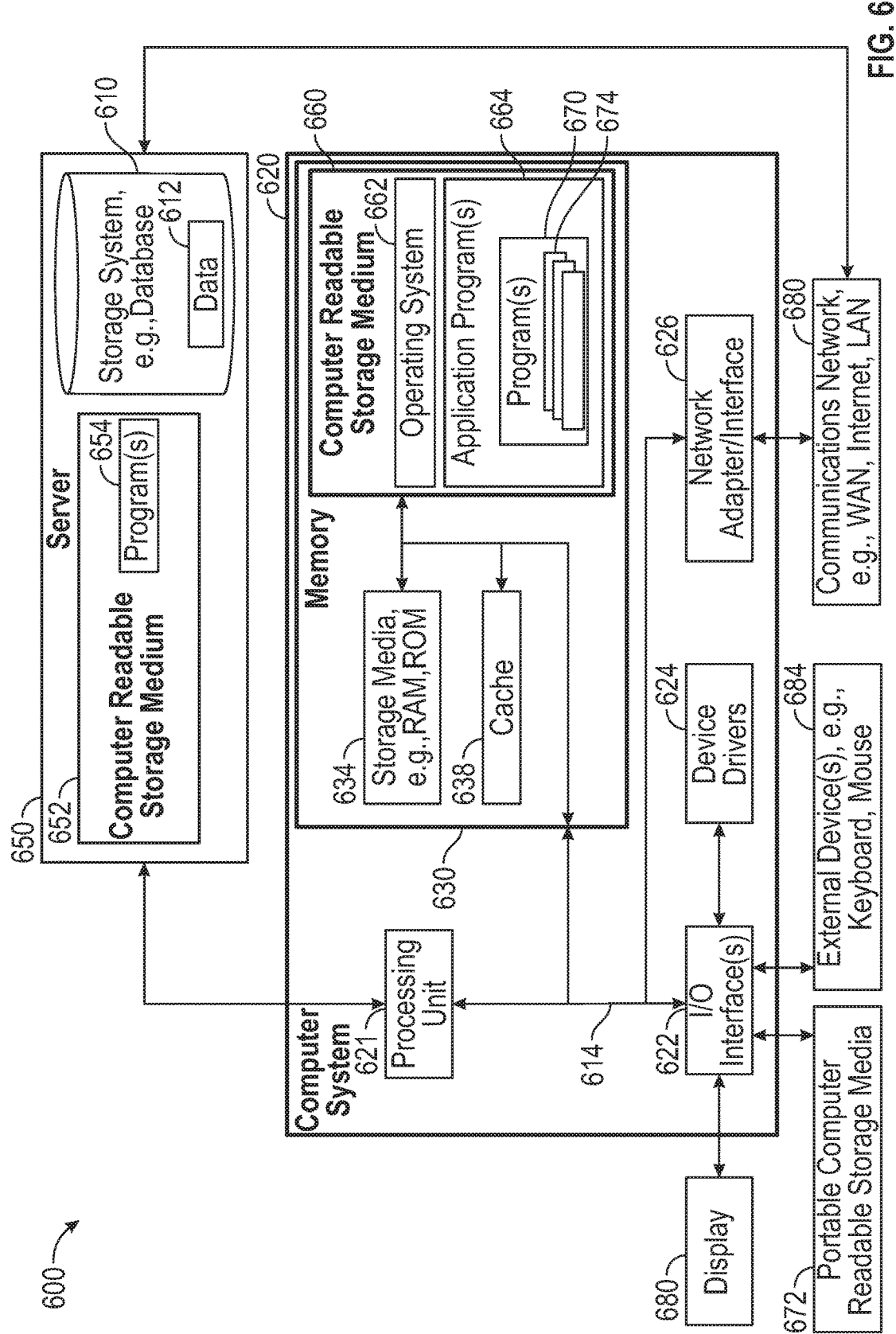
FIG. 6 illustrates an exemplary computer device in accordance with at least one embodiment of the present disclosure.

FIG. 6 illustrates a computer system 600 that can execute one or more flows of the present disclosure, including the flows of FIGS. 3A, 3B, 4A, 4B and 5. The components of the computer 620 may include, but are not limited to, one or more processors or processing units 621, a system memory 630, and a bus 614 that couples various system components including system memory 630 to processing unit 621.

The bus 614 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer 620 typically includes a variety of computer readable media. Such media may be any available media that is accessible by the computer 620 (e.g., computer system, or server), and can include both volatile and non-volatile media, as well as, removable and non-removable media.

Computer memory 630 can include additional computer readable storage media 634 in the form of volatile memory, such as random access memory (RAM) and/or cache memory 638. The computer 620 may further include other removable/non-removable, volatile/non-volatile computer storage media, in one example, portable computer readable storage media 672. In one embodiment, a computer readable storage medium 660 can be provided for reading from and writing to a non-removable, non-volatile magnetic media. The computer readable storage medium 660 can be embodied, for example, as a hard drive. Additional memory and data storage can be provided, for example, as a storage system (e.g., a database 610) for storing data 612 and communicating with the processing unit 621. The database can be stored on or part of a server 650. Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 614 by one or more data media interfaces. As will be further depicted and described below, memory 630 may include at least one program product which can include one or more program modules that are configured to carry out the functions of embodiments of the present disclosure.

One or more computer programs can generically be referred to as a program 670. The program 670 can include program modules 674. By way of example, the memory 630 may store an operating system 662, an application program 664, other program modules, and program data. The program modules 674 can generally carry out functions and/or methodologies of embodiments of the present disclosure as described herein, including flows 300A, 300B, 400A, 400B and 500. The one or more programs 670 are stored in memory 630 and are executable by the processing unit 621. It is understood that the operating system 662 and application program 664 stored on the computer readable storage medium 660 are similarly executable by the processing unit 621.

The computer 620 may also communicate with one or more external devices 1074 such as a keyboard, a pointing device, a display 680a, etc.; one or more devices that enable a user to interact with the computer 620; and/or any devices (e.g., network card, modem, etc.) that enables the computer 620 to communicate with one or more other computing devices. Such communication can occur via Input/Output (I/O) interfaces 622. Still yet, the computer 620 can communicate with one or more networks 680 such as a local area network (LAN), a general wide area network (WAN), and/or a public network (e.g., the Internet) via network adapter/interface 626. As depicted, network adapter 626 communicates with the other components of the computer 620 via bus 614. It should be understood that although not shown, other hardware and/or software components could be used in conjunction with the computer 1010. Examples, include, but are not limited to: microcode, device drivers 1024, redundant processing units, and external disk drive arrays, RAID systems, tape drives, and data archival storage systems, etc.

The flows of the present disclosure, e.g. 300A (FIG. 3A) may be embodied in a program 670 (FIG. 6) embodied on a computer readable storage device, for example, generally referred to as memory 630, and can more specifically refer to computer readable storage medium 660, as shown in FIG. 6. The program 670 is executable by the processing unit 621 of the computer 620 (to execute program steps, code, or program code). Additional data storage may also be embodied as the database 610 which includes data 612. The program or executable instructions may be offered as a service by a provider. The computer 620 and program 670 shown in FIG. 6 are generic representations of a computer and program that may be local to a user, or provided as a remote service (for example a cloud based service), and may be provided in further examples, using a website accessible using a network 680 (e.g., interacting with a network, the Internet, or cloud services). It is understood that the computer 620 and computer system 600 also generically represents herein a computer device or a computer included in a device, such as a laptop or desktop computer, etc., or one or more servers, alone or as part of a datacenter. The computer and computer system can include the network adapter/interface 626, and the input/output (I/O) interface(s) 622. The I/O interface 622 allows for input and output of data with an external device 684 that may be connected to the computer system. The network adapter/interface 626 may provide communications between the computer system and a computer network generically shown as the network 680. The method steps and system components and techniques may be embodied in modules of the program 670 for performing the tasks of each of the steps of the method and system, which are generically represented in FIG. 3A, FIG. 3B, FIG. 4, and FIG. 5 as program modules 674. The program 670 and program modules 674 can execute specific steps, routines, sub-routines, instructions or code, of the program. The method of the present disclosure can be run locally on a device such as a mobile device, or can be run a service, for instance, on the server 650 which may be remote and can be accessed using the communications network 680.

It is understood that a computer or a program running on the computer 620 may communicate with a server, herein embodied as the server 650, via one or more communications networks, herein embodied as the network 680. The communications network 680 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood that a computer or a program running on the computer 620 may communicate with a server, herein embodied as the server 650, via one or more communications networks, herein embodied as the network 680. The communications network 680 may include transmission media and network links which include, for example, wireless, wired, or optical fiber, and routers, firewalls, switches, and gateway computers. The communications network may include connections, such as wire, wireless communication links, or fiber optic cables. A communications network may represent a worldwide collection of networks and gateways, such as the Internet, that use various protocols to communicate with one another, such as Lightweight Directory Access Protocol (LDAP), Transport Control Protocol/Internet Protocol (TCP/IP), Hypertext Transport Protocol (HTTP), Wireless Application Protocol (WAP), etc. A network may also include a number of different types of networks, such as, for example, an intranet, a local area network (LAN), or a wide area network (WAN).

In one example, a computer can use a network which may access a website on the Web (World Wide Web) using the Internet. In one embodiment, a computer, including a mobile device, can use a communications system or network 680 which can include the Internet, or a public switched telephone network (PSTN), for example, a cellular network. The PSTN may include telephone lines, fiber optic cables, microwave transmission links, cellular networks, and communications satellites. The Internet may facilitate numerous searching and texting techniques, for example, using a cell phone or laptop computer to send queries to search engines via text messages (SMS), Multimedia Messaging Service (MMS) (related to SMS), email, or a web browser. The search engine can retrieve search results, that is, links to websites, documents, or other downloadable data that correspond to the query, and similarly, provide the search results to the user via the device as, for example, a web page of search results.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software service, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In one or more embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A method for charging an electronic device, comprising:
    monitoring activity of a user to estimate an amount of power generated by piezoelectric fabric disposed in an article of clothing worn by the user, the piezoelectric fabric being configured to generate electrical energy in response to movement of the user and the generated electrical energy being stored in a power supply device, and the power supply device being configured to provide power to a charging coil disposed in the article of clothing for charging the electronic device;
    selecting a user exercise predicted to generate sufficient power using the piezoelectric fabric to reach a threshold power level, in response to determining the estimated power is insufficient to charge the electronic device to the threshold power level; and
    outputting a prompt on the electronic device to advise the user to perform the user exercise.

2. The method of claim 1, wherein the article of clothing includes a plurality of coils stitched into the article of clothing, the plurality of coils being electrically coupled to the power supply device.

3. The method of claim 1, wherein determining that the estimated power is insufficient to charge the electronic device to the threshold power level comprises:
    analyzing the user activity to determine a contact position for the electronic device; and
    predicting whether the user activity is sufficient to charge the electronic device to the threshold power level when the electronic device has a power level below a certain threshold.

4. The method of claim 1, wherein the user is one of a plurality of users, wherein the electronic device is one of a plurality of electronic devices, the clothing is part of a plurality of articles of clothing, the user activity includes activity data for each one of the plurality of users, and the method comprises:
    collecting data related to associated activity of each of the plurality of users from at least one data source comprising: i) a social media profile of each of the plurality of users, ii) a data source containing a shopping history for each of the plurality of users, or iii) survey data collected from of each of the plurality of users.

5. The method of claim 4, wherein the method further comprises:
   analyzing the user activity to identify patterns for at least two sets of the plurality of users, wherein the patterns comprise at least one of: i) a professional pattern, ii) a hobby pattern, and iii) a preference pattern; and
   creating one or more user profiles based on the patterns.

6. The method of claim 5, wherein at least one charging coils is disposed on each one of the plurality of articles of clothing, wherein the method further comprises:
   selecting a location for each of the plurality of charging devices on the plurality of articles of clothing based on the one or more user profiles, a first article of clothing of the plurality of articles of clothing having a first distribution of charging devices based on a first user profile, and a second article of clothing of the plurality of articles of clothing having a second distribution of charging devices based on a second user profile.

7. The method of claim 6, wherein the method further comprises:
   creating a first set of customer segments based on the first user profile;
   creating a second set of customer segments based on the second user profile;
   providing an advertisement to a first plurality of customers for the first article of clothing, the first plurality of customers relating to the first user profile; and
   providing a second advertisement to a second plurality of customers for the second article of clothing, the second plurality of customer relating to the second user profile.

8. A system, comprising:
   a processor; and
   memory storing an application, which, when executed by the processor, performs an operation for charging an electronic device based on user movement, the operation comprising:
      monitoring activity of a user to estimate an amount of power generated by piezoelectric fabric disposed in an article of clothing worn by the user, the piezoelectric fabric being configured to generate electrical energy in response to movement of the user and the generated electrical energy being stored in a power supply device, and the power supply device being configured to provide power to a charging coil disposed in the article of clothing for charging the electronic device;
      selecting a user exercise predicted to generate sufficient power using the piezoelectric fabric to reach a threshold power level, in response to determining the estimated power is insufficient to charge the electronic device to the threshold power level; and
      outputting a prompt on the electronic device to advise the user to perform the user exercise.

9. The system of claim 8, wherein the article of clothing includes a plurality of coils stitched into the article of clothing, and the plurality of coils is electrically coupled to the power supply device.

10. The system of claim 8, wherein determining that the estimated power is insufficient to charge the electronic device to a threshold power level comprises:
   analyzing the user activity to determine a contact position for the electronic device; and
   predicting whether the user activity is sufficient to charge the electronic device to the threshold power level when the electronic device has a power level below a certain threshold.

11. The system of claim 8, wherein the user is one of a plurality of users, the electronic device is one of a plurality of electronic devices, the clothing is part of a plurality of articles of clothing, the user activity includes activity data for each one of the plurality of users, and the operation comprises:
   collecting data related to associated activity of each of the plurality of users from at least one data source comprising: i) a social media profile of each of the plurality of users, ii) a data source containing a shopping history for each of the plurality of users, or iii) survey data collected from of each of the plurality of users.

12. The system of claim 11, wherein the operation further comprises:
   analyzing the user activity to identify patterns for at least two sets of the plurality of users, wherein the patterns comprise at least one of: i) a professional pattern, ii) a hobby pattern, and iii) a preference pattern; and
   creating one or more user profiles based on the patterns.

13. The system of claim 12, wherein at least one of charging coil is disposed on each one of the plurality of articles of clothing, the operation further comprises:
   selecting a location for each of the plurality of charging devices on the plurality of articles of clothing based on the one or more user profiles, a first article of clothing of the plurality of articles of clothing having a first distribution of charging devices based on a first user profile, and a second article of clothing of the plurality of articles of clothing having a second distribution of charging devices based on a second user profile.

14. The system of claim 13, wherein the operation further comprises:
   creating a first set of customer segments based on the first user profile;
   creating a second set of customer segments based on the second user profile;
   providing an advertisement to a first plurality of customers for the first article of clothing, wherein the first plurality of customers relates to the first user profile; and
   providing a second advertisement to a second plurality of customers for the second article of clothing, wherein the second plurality of customer relates to the second user profile.

15. A computer program product for charging an electronic device based on user movement, the computer program product comprising:
   a computer-readable storage medium having computer-readable program code embodied therewith, the computer-readable program code executable by one or more computer processors to:
      monitor activity of a user to estimate an amount of power generated by piezoelectric fabric disposed in an article of clothing worn by the user, the piezoelectric fabric being configured to generate electrical energy in response to movement of the user and the generated electrical energy being stored in a power supply device, and the power supply device being configured to provide power to a charging coil disposed in the article of clothing for charging the electronic device;
      select a user exercise predicted to generate sufficient power using the piezoelectric fabric to reach a threshold power level, in response to determining the estimated power is insufficient to charge the electronic device to the threshold power level; and output a prompt on the electronic device to advise the user to perform the user exercise.

16. The computer program product of claim 15, wherein the article of clothing includes a plurality of coils stitched into the article of clothing, wherein the plurality of coils is electrically coupled to the power supply device.

17. The computer program product of claim 16, wherein the user is one of a plurality of users, the electronic device is one of a plurality of electronic devices, the clothing is part of a plurality of articles of clothing, the user activity includes activity data for each one of the plurality of users, and wherein the computer-readable program code is executable to:

collect data related to associated activity of each of the plurality of users from at least one data source comprising: i) a social media profile of each of the plurality of users, ii) a data source containing a shopping history for each of the plurality of users, and iii) survey data collected from of each of the plurality of users.

18. The computer program product of claim 15, wherein determining that the estimated power is insufficient to charge the electronic device to the threshold power level comprises:

analyzing the user activity to determine a contact position for the electronic device; and predicting whether the user activity is sufficient to charge the electronic device to the threshold power level when the electronic device has a power level below a certain threshold.

19. The computer program product of claim 18, wherein the computer-readable program code is executable to:

analyze the user activity to identify patterns for at least two sets of the plurality of users, wherein the patterns comprise at least one of: i) a professional pattern, ii) a hobby pattern, and iii) a preference pattern; and create one or more user profiles based on the patterns.

20. The computer program product of claim 19, wherein at least one charging coil is disposed on each one of the plurality of articles of clothing, the computer-readable program code is executable to:

select a location for each of the plurality of charging devices on the plurality of articles of clothing based on the one or more user profiles, a first article of clothing of the plurality of articles of clothing having a first distribution of charging devices based on a first user profile, and a second article of clothing of the plurality of articles of clothing having a second distribution of charging devices based on a second user profile.

* * * * *